United States Patent
Milacic

(10) Patent No.: US 7,654,128 B2
(45) Date of Patent: Feb. 2, 2010

(54) GAS ANALYZING APPARATUS AND METHOD

(75) Inventor: Milos Milacic, New Boston, MI (US)

(73) Assignee: Ford Motor Company, Dearborn, MI (US)

( * ) Notice: Subject to any disclaimer, the term of this patent is extended or adjusted under 35 U.S.C. 154(b) by 745 days.

(21) Appl. No.: 11/318,143

(22) Filed: Dec. 23, 2005

(65) Prior Publication Data

US 2007/0148510 A1 Jun. 28, 2007

(51) Int. Cl.
*G01N 7/00* (2006.01)

(52) U.S. Cl. .................................... 73/23.2

(58) Field of Classification Search ............... 73/23.2, 73/23.24
See application file for complete search history.

(56) References Cited

U.S. PATENT DOCUMENTS

| | | | |
|---|---|---|---|
| 5,623,597 A * | 4/1997 | Kikinis | 726/18 |
| 6,429,019 B1 | 8/2002 | Goldstein et al. | |
| 6,640,626 B2 * | 11/2003 | Saikalis et al. | 73/204.11 |
| 6,881,507 B2 | 4/2005 | Milacic | |
| 2003/0157383 A1 | 8/2003 | Takahashi | |

* cited by examiner

*Primary Examiner*—Hezron Williams
*Assistant Examiner*—Alex Devito
(74) *Attorney, Agent, or Firm*—Tung & Associates

(57) ABSTRACT

A gas analyzing apparatus for analyzing gas composition in a multi-gas stream is disclosed. The gas analyzing apparatus includes a plurality of sensors adapted to sense a characteristic of the gases and a microprocessor connected to the plurality of sensors and adapted to determine actual rates of flow of the gases. A method of analyzing a composition of a gas stream and a fuel cell system are also disclosed.

17 Claims, 2 Drawing Sheets

GAS ANALYZING APPARATUS AND METHOD

FIELD

The present invention relates to apparatuses and methods for analyzing the composition of a gas. More particularly, the present invention relates to a gas analyzing apparatus and method which is suitable for analyzing the composition of a gas in an anode of a fuel cell system.

BACKGROUND

During the operation of a fuel cell, there exists in the anode stream of the anode loop water vapor, nitrogen and residual gases such as argon, for example, in addition to a fuel gas such as hydrogen. The rates of flow of each of these gases in the anode stream can be used to determine the composition of the gases in the anode stream. This information can be used to determine the need to purge the anode loop of the fuel cell, to increase or decrease humidification of the anode loop, and adjust the intake of fuel into a fuel cell stack. Conventional thermal mass flow sensors can be calibrated to measure the flow rates of two gases in a common gas stream. However, for purposes of determining the composition of gases in an anode gas stream of a fuel cell, conventional thermal mass flow sensors are largely insufficient.

SUMMARY

The present invention is generally directed to a gas analyzing apparatus for analyzing a composition of a gas stream. The gas analyzing apparatus includes a plurality of sensors adapted to sense a characteristic of the gases and a microprocessor connected to the plurality of sensors and adapted to determine actual rates of flow of the gases. The invention is further directed to a method of analyzing individual gases in a gas stream and to a fuel cell system.

BRIEF DESCRIPTION OF THE DRAWINGS

The invention will now be described, by way of example, with reference to the accompanying drawings, in which.

DETAILED DESCRIPTION

Figure 1:
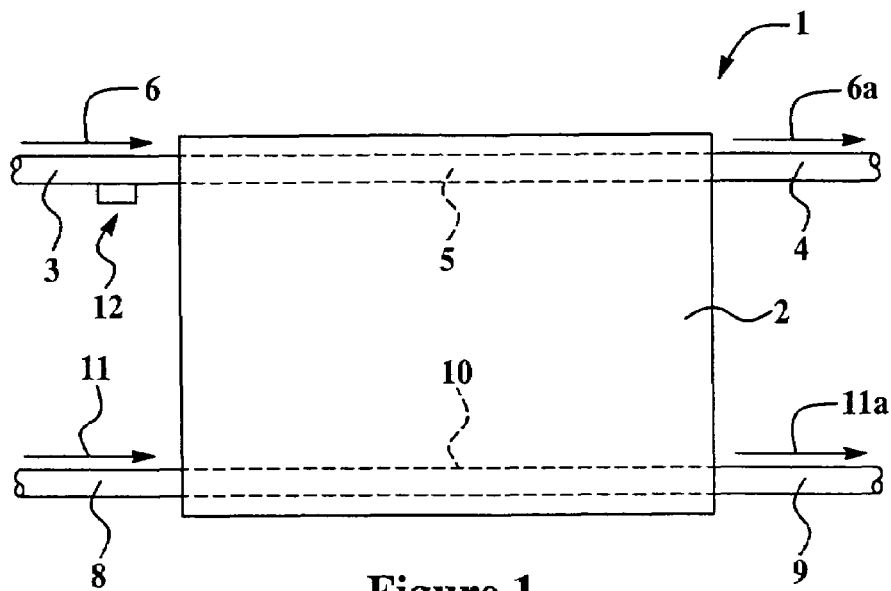
FIG. 1 is a schematic view of a fuel cell system in implementation of an illustrative embodiment of an anode gas analyzing apparatus and method according to the present invention.

Referring initially to FIG. 1, an illustrative embodiment of a fuel cell system which is suitable for implementation of the present invention is generally indicated by reference numeral 1. The fuel cell system 1 includes a fuel cell stack 2 having an anode inlet 3 which distributes an anode stream 6 containing a fuel gas, typically hydrogen, into the fuel cell stack 2. The anode stream 6 typically further includes various residual gases such as nitrogen and water vapor, for example. A cathode inlet 8 distributes a cathode stream 11 containing an oxidant gas, typically oxygen, into the fuel cell stack 2. An anode outlet 4 distributes excess fuel gas 6a, and a cathode outlet 9 distributes excess oxidant gas with exhaust water 11a, from the fuel cell stack 2.

In operation of the fuel cell stack 2, an anode loop 5 (shown in phantom) distributes the anode gas stream 6 through the anode side of the fuel cell stack 2. A cathode loop 10 (shown in phantom) distributes the cathode gas stream 11 through the cathode side of the fuel cell stack 2. At the anode side, electrons are harvested from the fuel gas in the anode stream 6 and distributed through an external circuit (not shown) which drives a motor (not shown). The protons from the fuel gas in the cathode stream 11 are distributed through a membrane (not shown) to the cathode side. The electrons are distributed from the external circuit to the cathode side of the fuel cell stack 2, where they are combined with the protons from the membrane to form water. The excess oxidant gas with exhaust water 11a is distributed from the fuel cell stack 2 through the cathode outlet 9.

Figure 2:
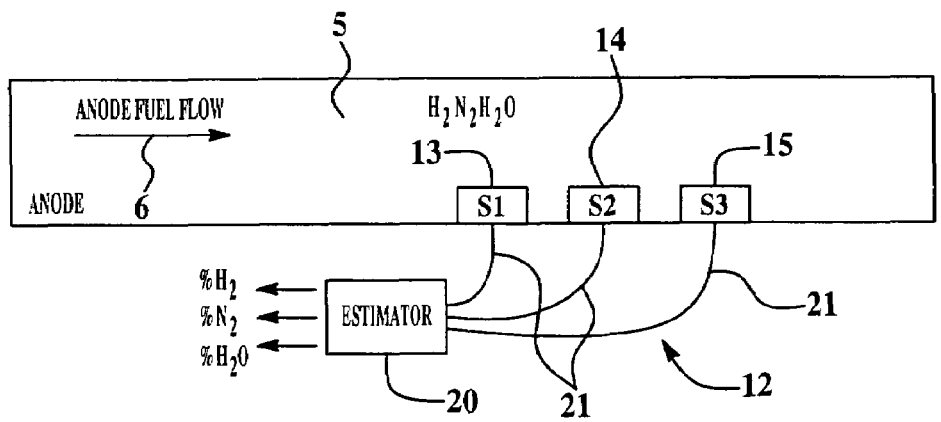
FIG. 2 is a schematic view of a portion of an anode loop in a fuel cell system, with an illustrative embodiment of an anode gas analyzing apparatus according to the present invention integrated into the anode loop of a fuel cell system.

As shown in FIG. 2, an illustrative embodiment of a gas analyzing apparatus according to the present invention is generally indicated by reference numeral 12. The gas analyzing apparatus 12 is suitably adapted to sense a characteristic of each of multiple gases in the anode stream 6 of the fuel cell stack 2 to determine the compositions of the gases (which may be expressed as a percentage of each gas in the anode stream 6) based on the characteristic of the gas. For example, the gas analyzing apparatus 12 may be adapted to measure the rates of flow of multiple gases in the anode stream 6 of the fuel cell stack 2 and interpolate the compositions of the gases based on the rates of flow. The gas analyzing apparatus 12 includes a sensor 13, a sensor 14 and a sensor 15 which are incorporated into the anode loop 5, as shown, of the fuel cell system 1. Alternatively or additionally, the sensor 13, sensor 14 and sensor 15 may be incorporated into the anode inlet 3 of the fuel cell stack 2, as shown in FIG. 1.

Each of the sensor 13, the sensor 14 and the sensor 15 is adapted to sense a characteristic of two different gases in the anode stream 6. For example, the sensor 13, the sensor 14 and the sensor 15 may be calibrated to measure estimated rates of flow of two different gases in the anode stream 6. The sensor 13 is calibrated to measure the estimated rates of flow of a first gas and a second gas, the sensor 14 is calibrated to measure the estimated rates of flow of the first gas and a third gas, and the sensor 15 is calibrated to measure the estimated rates of flow of the second gas and the third gas. For example, the sensor 13 may be calibrated to measure the estimated rates of flow of hydrogen and nitrogen; the sensor 14 may be calibrated to measure the estimated rates of flow of hydrogen and water; and the sensor 15 may be calibrated to measure the estimated rates of flow of water and nitrogen in the anode stream 6. Because the anode stream 6 includes a fuel gas such as hydrogen as well as other gases such as nitrogen and water vapor, the estimated flow rates for these gases as measured by the sensor 13, sensor 14 and sensor 15 differ from each other. Therefore, the actual flow rates of the gases must be determined in order to obtain the compositions of the gases in the anode stream 6. The actual rates of hydrogen flow, nitrogen flow and water flow in the anode stream 6 are different functions of the rates of flow of the gases as measured by the sensor 13 (S1), the sensor 14 (S2) and the sensor 15 (S3), as follows:

$H_2$ flow=F1 (S1$H_2$, S1$N_2$, S2$H_2O$, S2$H_2$, S3$N_2$, S3$H_2O$)
$N_2$ flow=F2 (S1$H_2$, S1$N_2$, S2$H_2O$, S2$H_2$, S3$N_2$, S3$H_2O$)
$H_2O$ flow=F3 (S1$H_2$, S1$N_2$, S2$H_2O$, S2$H_2$, S3$N_2$, S3$H_2O$)

The functions F1, F2 and F3 can be determined empirically, by using spectroscopy, for example, to calibrate the sensor 13, sensor 14 and sensor 15. Additionally, humidity sensors (not shown), pressure sensors and/or temperature sensors (not shown) can be used to dynamically tune F1, F2 and F3 using humidity, pressure and/or temperature values, respectively, of the anode stream 6. While the sensor 13, the sensor 14 and the sensor 15 shown in FIG. 2 are three in number, it is to be understood that the sensors may be two or more in number depending on the number of gases which are in the anode stream 6 and the compositions of which are to be determined.

A microprocessor 20 is connected to the sensor 13, the sensor 14 and the sensor 15, typically through wiring 21. The microprocessor 20 has the capability of receiving a characteristic of the gases in the anode stream 6 as sensed by the sensor 13, the sensor 14 and the sensor 15 and using this characteristic to determine the actual flow rates of the respective gases in the anode stream 6. For example, the microprocessor 20 may have the capability to receive the estimated flow rates of the gases as measured by each of the first sensor 13, the second sensor 14 and the third sensor 15, and determine the actual flow rates of the gases using various functions of the measured flow rates. The actual flow rates of the gases as determined by the microprocessor 20 can be used to determine the compositions of the gases, typically by percentage of the total, in the anode stream 6. This may be accomplished by, for example, formulating a look-up table in which the actual flow rates of the gases in the anode stream 6 are interpolated to the percentage composition of the gases in the anode stream 6. Alternatively, the microprocessor 20 may include the capability to interpolate the flow rates of the gases to determine the percentage compositions of the gases in the anode stream 6 using trained neural network software, for example.

Figure 3:
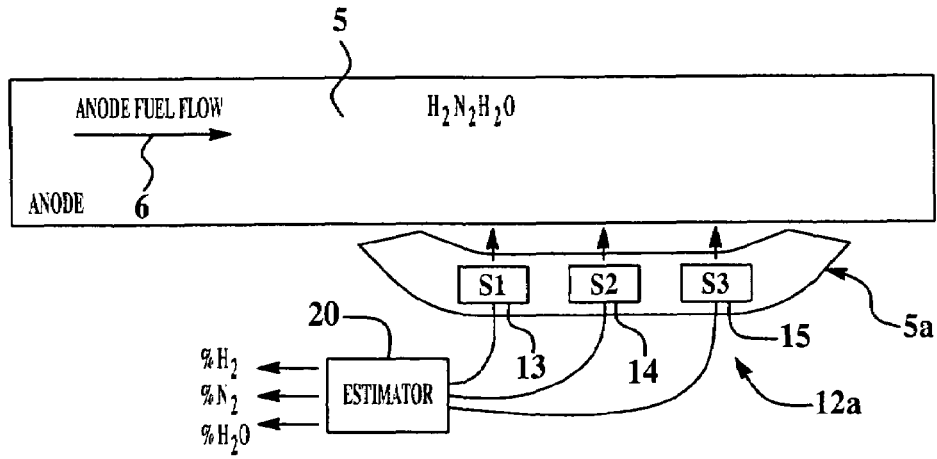
FIG. 3 is a schematic view of a portion of an anode loop in a fuel cell system, with a stand-alone diagnostic unit embodiment of an anode gas analyzing apparatus according to the present invention detached from an anode loop of a fuel cell system.

Referring next to FIG. 3, an alternative embodiment of a gas analyzing apparatus according to the present invention is generally indicated by reference numeral 12a. The gas analyzing apparatus 12a may be similar in design and function to the gas analyzing apparatus 12 which was heretofore described with respect to FIG. 2, except the gas analyzing apparatus 12a is configured as a stand-alone diagnostic unit rather than being incorporated into the anode loop 5, as shown, or anode inlet 3 of the fuel cell system 1, as was the case with regard to the gas analyzing apparatus 12. Accordingly, the sensing head 5a containing sensor 13, sensor 14 and sensor 15 may be detachable with respect to at least one of the anode loop 5 and the anode inlet 3, according to the knowledge of those skilled in the art, to place the sensor 13, sensor 14 and sensor 15 in the path of the anode stream 6 in order to measure the estimated flow rates or other characteristic of the fuel gas and residual gases in the anode stream 6, typically in the same manner as was heretofore described with respect to the gas analyzing apparatus 12 of FIG. 2.

Figure 4:
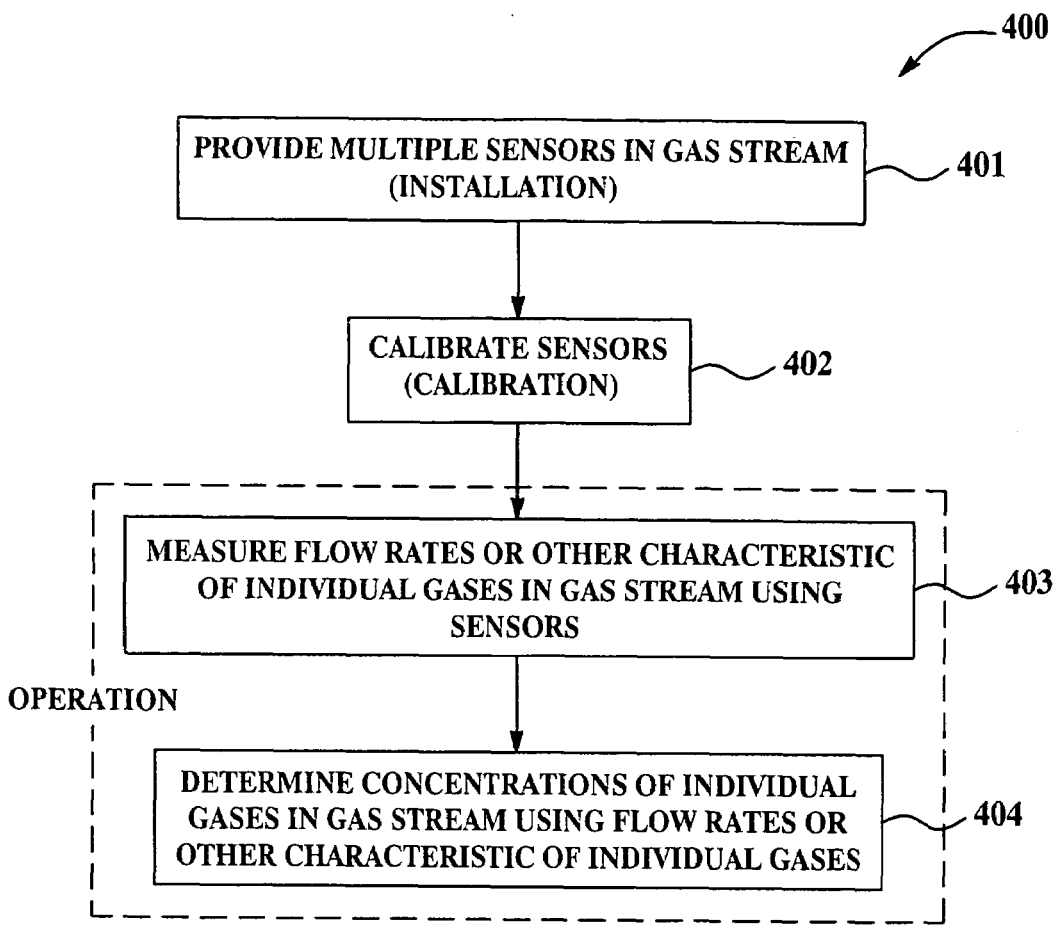
FIG. 4 is a flow diagram illustrating steps in implementation of an anode gas analyzing method according to the present invention.

Referring to the flow diagram of FIG. 4 in conjunction with FIGS. 1 and 2, a flow diagram 400 illustrating typical operation of the gas analyzing apparatus 12 in implementation of an anode gas analyzing method according to the present invention is shown. In step 401, the sensors 13, 14 and 15 are provided in a gas stream such as the anode stream 6 of an operating fuel cell system 1, for example. This may be carried out by incorporating the sensors 13, 14 and 15 into the anode loop 5 or anode inlet 3, for example, of a fuel cell system 1, as was heretofore described with respect to the gas analyzing apparatus 12 of FIG. 2. Alternatively, the sensors 13, 14 and 15 may be detachably associated with the anode loop 5 or anode inlet 3 of the fuel cell system 1, as was heretofore described with respect to the stand-alone diagnostic unit embodiment of the gas analyzing apparatus 12a of FIG. 3.

In step 402, the sensors 13, 14 and 15 are calibrated to sense a characteristic of each of the individual gases in the anode stream 6 or other gas stream. For example, the sensors 13, 14 and 15 may be calibrated to measure the estimated flow rates of individual gases in the anode stream 6 or other gas stream. The sensors 13, 14 and 15 may be calibrated to measure the estimated flow rates of first and second gases, first and third gases and second and third gases, respectively, in the anode stream 6 or other gas stream. For example, the sensor 13 may be calibrated to measure the estimated flow rates of hydrogen and nitrogen; the sensor 14 may be calibrated to sense the estimated flow rates of hydrogen and water vapor; and the sensor 15 may be calibrated to sense the estimated flow rates of nitrogen and hydrogen in the anode stream 6 or other gas stream. Calibration of the sensor 13 (S1), sensor 14 (S2) and sensor 15 (S3) may be accomplished by, for example, determining different functions (F1, F2 and F3) of the flow rates of the individual gases empirically, such as by using spectroscopy, for example, as follows:

$H_2$ flow=F1 (S1$H_2$, S1$N_2$, S2$H_2O$, S2$H_2$, S3$N_2$, S3$H_2O$)
$N_2$ flow=F2 (S1$H_2$, S1$N_2$, S2$H_2O$, S2$H_2$, S3$N_2$, S3$H_2O$)
$H_2O$ flow=F3 (S1$H_2$, S1$N_2$, S2$H_2O$, S2$H_2$, S3$N_2$, S3$H_2O$)

Additionally, humidity sensors, pressure sensors and/or temperature sensors can be placed in the anode stream 6 or other gas stream to refine F1, F2 and F3 using humidity, pressure and/or temperature values, respectively, of the anode stream 6 or other gas stream.

In step 403, during functioning of the fuel cell system 1 or other system, the sensor 13, sensor 14 and sensor 15 measure a characteristic, such as the estimated flow rates of the individual gases in the anode stream 6 or other gas stream, for example. Values indicating the estimated flow rates for the gases, as determined by the sensors 13, 14 and 15, are transmitted to the microprocessor 20, which determines the actual flow rates of the gases using the various functions of the rates of flow of the gases. For example, the microprocessor 20 may determine the actual flow rates of hydrogen gas, nitrogen gas and water vapor in the anode stream 6 or other gas stream using the functions F1, F2 and F3, respectively.

In step 404, the concentrations of the gases in the anode stream 6 or other gas stream are determined using the actual flow rates or other characteristic of the individual gases as determined in step 403. These concentrations may be determined by, for example, formulating a look-up table in which the actual flow rates of the gases in the anode stream 6 or other gas stream are interpolated to the percentage compositions of the gases in the anode stream 6. The concentrations of the gases may alternatively be determined by interpolating the actual flow rates of the gases to the percentage compositions of the gases in the anode stream 6 or other gas stream using trained neural network, for example. The flow rates and concentrations of the individual gases in the anode stream 6 or other gas stream can be used, for example, to determine the need to purge the anode loop 5 of the fuel cell stack 2; to increase or decrease humidification of the anode loop 5; and/or to adjust the intake of fuel gas into the fuel cell stack 2, as needed.

Figure 5:
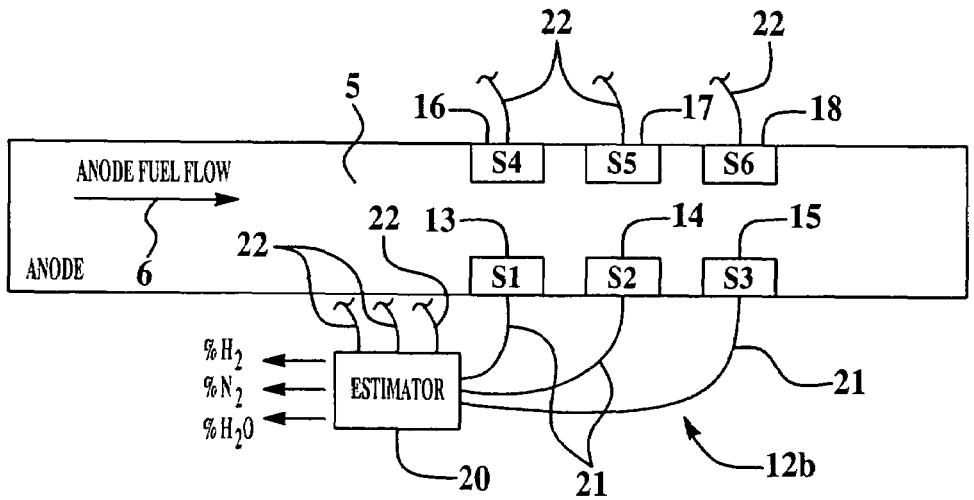
FIG. 5 is a schematic view of a portion of an anode loop in a fuel cell system, with an alternative embodiment of an anode gas analyzing apparatus according to the present invention connected to the anode loop.

Referring next to FIG. 5, an alternative embodiment of the gas analyzing apparatus, which is generally indicated by reference numeral 12b. The gas analyzing apparatus 12b is similar in design to the gas analyzing apparatus 12 which was heretofore described with respect to FIG. 2, except the gas analyzing apparatus 12b includes additional sensors 16, 17 and 18 which are connected to the microprocessor 20 such as by wiring 22, respectively. The sensor 16, sensor 17 and sensor 18 are adapted to sense a characteristic, such as an estimated flow rate, for example, of each of multiple gases which are present in the anode stream 6 in addition to the gases the characteristic of each of which is measured by the sensors 13, 14 and 15. The sensor 16, sensor 17 and sensor 18 may each be adapted to measure the estimated flow rates of two gases. For example, the sensor 16 may be adapted to measure the estimated flow rates of argon and hydrogen; the sensor 17 may be adapted to measure the estimated flow rates of argon and nitrogen; and the sensor 18 may be adapted to measure the estimated flow rates of argon and water vapor. Therefore, in operation of the fuel cell system 1, the microprocessor 20 is capable of determining the actual flow rate of argon in the anode stream 6, in addition to the actual flow rates of hydrogen, nitrogen and water, typically in the same manner as was heretofore described with respect to FIGS. 1, 2 and 4. This facilitates determination of the concentration of argon in the anode stream 6 using a look-up table or trained neural network software, for example, as well as enhances the accuracy of the actual flow rate and concentration measurements for hydrogen, nitrogen and water vapor in the anode stream 6.

While the preferred embodiments of the invention have been described above, it will be recognized and understood that various modifications can be made in the invention and the appended claims are intended to cover all such modifications which may fall within the spirit and scope of the invention.

What is claimed is:

1. A method of analyzing a plurality of individual gases in a gas stream, comprising:
   determining characteristics of said individual gases, respectively in said gas stream;
   determining actual rates of flow of said individual gases, respectively, in said gas stream based on said characteristics; and
   determining concentrations of said individual gases, respectively, in said gas stream based on said actual rates of flow of each of said individual gases in said gas stream, each individual gas concentration in said gas stream determined as a proportional concentration of a total concentration of gases comprising said gas stream.

2. The method of claim 1 wherein said determining characteristics of said individual gases, respectively, comprises measuring estimated rates of flow of said individual gases, respectively.

3. The method of claim 1 wherein said determining concentrations of said individual gases, respectively, in said gas stream comprises interpolating said actual rates of flow of said individual gases, respectively, in said gas stream with said concentrations of said individual gases.

4. The method of claim 3 wherein said interpolating said actual rates of flow of said individual gases in said gas stream with said concentrations of said individual gases comprises formulating a lookup table.

5. The method of claim 3 wherein said interpolating said actual rates of flow of said individual gases in said gas stream with said concentrations of said individual gases comprises using a trained neural network.

6. The method of claim 1 wherein said determining characteristics of said individual gases, respectively, comprises providing a plurality of sensors in said gas stream and measuring estimated rates of flow of said individual gases, respectively, in said gas stream.

7. The method of claim 6 wherein said providing a plurality of sensors in said gas stream comprises providing first, second and third sensors in said gas stream and wherein said measuring estimated rates of flow of said individual gases, respectively, in said gas stream comprises measuring estimated rates of flow of hydrogen and nitrogen, hydrogen and water vapor, and nitrogen and water vapor in said gas stream using said first, second and third sensors, respectively.

8. The method of claim 7 further comprising providing fourth, fifth and sixth sensors in said gas stream and measuring estimated rates of flow of argon and hydrogen, argon and nitrogen and argon and water vapor in said gas stream using said fourth, fifth and sixth sensors, respectively.

9. A method of analyzing individual gases in a gas stream, comprising:
   determining characteristics of said individual gases, respectively;
   determining actual rates of flow of said individual gases, respectively, in said gas stream based on said characteristics; and
   determining concentrations of said individual gases, respectively, in said gas stream based on said actual rates of flow of said individual gases in said gas stream;
   wherein said determining characteristics of said individual gases, respectively, comprises providing a plurality of sensors in said gas stream and measuring estimated rates of flow of said individual gases, respectively, in said gas stream; and,
   wherein said providing a plurality of sensors in said gas stream comprises providing first, second and third sensors in said gas stream and wherein said measuring estimated rates of flow of said individual gases, respectively, in said gas stream comprises measuring estimated rates of flow of hydrogen and nitrogen, hydrogen and water vapor, and nitrogen and water vapor in said gas stream using said first, second and third sensors, respectively.

10. The method of claim 9 wherein said determining concentrations of said individual gases, respectively, in said gas stream comprises interpolating said actual rates of flow of said individual gases, respectively, in said gas stream with said concentrations of said individual gases.

11. The method of claim 10 wherein said interpolating said actual rates of flow of said individual gases in said gas stream with said concentrations of said individual gases comprises formulating a look-up table.

12. The method of claim 11 wherein said interpolating said actual rates of flow of said individual gases in said gas stream with said concentrations of said individual gases comprises using a trained neural network.

13. A method of analyzing a plurality of individual gases in a gas stream, comprising:
   providing a plurality of sensors in said gas stream and measuring estimated rates of flow of said individual gases, respectively, in said gas stream;
   determining actual rates of flow of said individual gases, respectively, in said gas stream based on said estimated rates of flow of said individual gases; and
   determining concentrations of said individual gases, respectively, in said gas stream based on said actual rates of flow of each of said individual gases in said gas stream, each individual gas concentration in said gas stream determined as a proportional concentration of a total concentration of gases comprisinq said gas stream.

14. The method of claim 13 wherein said determining concentrations of said individual gases, respectively, in said gas stream comprises interpolating said actual rates of flow of said individual gases, respectively, in said gas stream with said concentrations of said individual gases.

15. The method of claim 14 wherein said interpolating said actual rates of flow of said individual gases in said gas stream with said concentrations of said individual gases comprises formulating a look-up table.

16. The method of claim 15 wherein said interpolating said actual rates of flow of said individual gases in said gas stream with said concentrations of said individual gases comprises using a trained neural network.

17. The method of claim 13 wherein said providing a plurality of sensors in said gas stream comprises providing first, second and third sensors in said gas stream and wherein said measuring estimated rates of flow of said individual gases, respectively, in said gas stream comprises measuring estimated rates of flow of hydrogen and nitrogen, hydrogen and water vapor, and nitrogen and water vapor in said gas stream using said first, second and third sensors, respectively.

* * * * *